(12) United States Patent
Yu et al.

(10) Patent No.: US 10,842,621 B2
(45) Date of Patent: Nov. 24, 2020

(54) ARTIFICIAL CARDIAC VALVE

(71) Applicant: SHANGHAI NEWMED MEDICAL CO., LTD., Shanghai (CN)

(72) Inventors: Qifeng Yu, Shanghai (CN); Haishan Wang, Shanghai (CN); Yuchen Liang, Shanghai (CN); Jingyu Chen, Shanghai (CN); Linan Chang, Shanghai (CN); Tao Qin, Shanghai (CN)

(73) Assignee: Shanghai Newmed Medical Co., Ltd., Zhanghai (CN)

( * ) Notice: Subject to any disclaimer, the term of this patent is extended or adjusted under 35 U.S.C. 154(b) by 90 days.

(21) Appl. No.: 16/329,675

(22) PCT Filed: Oct. 14, 2016

(86) PCT No.: PCT/CN2016/102199
§ 371 (c)(1),
(2) Date: Feb. 28, 2019

(87) PCT Pub. No.: WO2018/040244
PCT Pub. Date: Mar. 8, 2018

(65) Prior Publication Data
US 2019/0192293 A1    Jun. 27, 2019

(30) Foreign Application Priority Data

Aug. 31, 2016  (CN) .......................... 2016 1 0790804

(51) Int. Cl.
*A61F 2/24*        (2006.01)
(52) U.S. Cl.
CPC .......... *A61F 2/2418* (2013.01); *A61F 2/2409* (2013.01); *A61F 2220/0016* (2013.01);
(Continued)

(58) Field of Classification Search
CPC ......... A61F 2/24; A61F 2/2412; A61F 2/2418
(Continued)

(56) References Cited

U.S. PATENT DOCUMENTS 10,687,939 B2 *   6/2020  Cooper ................. A61F 2/2418
2017/0095328 A1 * 4/2017  Cooper ................. A61F 2/2418
(Continued)

FOREIGN PATENT DOCUMENTS

CN         103313734 A    9/2013
CN         104799974 A    7/2015
(Continued)

*Primary Examiner* — Suzette J Gherbi
(74) *Attorney, Agent, or Firm* — Muncy, Geissler, Olds & Lowe, P.C.

(57) ABSTRACT

An artificial cardiac valve is disclosed, which includes an outer stent; an inner stent nested within and connected to the outer stent; leaflets disposed inside the inner stent; and membranes attached to walls of the outer and inner stents. The inner stent is a cylindrical mesh tube, and the outer stent includes a first stent segment, a second stent segment and a third stent segment which are connected sequentially. The first stent segment is a mesh tube. The second stent is a mesh tube having a substantially D-shaped cross-section, and the third stent segment is a flared mesh tube. The first stent segment has a maximum diameter that is equal to a diameter of the second stent segment and to a minimum diameter of the third stent segment. In this stent design, the inner stent can withstand traction forces from the leaflets, and the outer stent is adapted to match the anatomy of the native valve. As a result, after release, the artificial cardiac valve will seldom experience displacement and be rarely associated with paravalvular leaks. Moreover, it has a prolonged service life.

9 Claims, 4 Drawing Sheets

(52) U.S. Cl.
CPC ............... *A61F 2230/0034* (2013.01); *A61F 2250/0039* (2013.01)

(58) Field of Classification Search
USPC .................................................. 623/2.1–2.19
See application file for complete search history.

(56) References Cited

U.S. PATENT DOCUMENTS

| | | | |
|---|---|---|---|
| 2019/0183642 A1* | 6/2019 | Tegels | A61F 2/2439 |
| 2019/0262134 A1* | 8/2019 | Dale | A61F 2/2418 |
| 2019/0274827 A1* | 9/2019 | Iobbi | A61F 2/2412 |
| 2020/0038180 A1* | 2/2020 | Oba | A61F 2/2433 |
| 2020/0146818 A1* | 5/2020 | Lane | A61F 2/2412 |
| 2020/0188091 A1* | 6/2020 | Lane | A61F 2/2436 |
| 2020/0222180 A1* | 7/2020 | Lane | A61F 2/2436 |

FOREIGN PATENT DOCUMENTS

| | | |
|---|---|---|
| CN | 105658180 A | 6/2016 |
| CN | 105726167 A | 7/2016 |
| CN | 205434001 U | 8/2016 |
| EP | 2606854 A1 | 6/2013 |
| WO | WO-2012/120953 A1 | 9/2012 |

\* cited by examiner

ARTIFICIAL CARDIAC VALVE

TECHNICAL FIELD

The present invention relates to the field of medical devices and, in particular, to an artificial cardiac valve.

BACKGROUND

The heart is a very important organ of the human body, which powers the human blood circulation. The heart is divided into left and right parts, each containing a ventricle and an atrium. The ventricles are separated from each other by the interventricular septum and the atria are separated from each other by the interatrial septum. In addition, there are valves for preventing blood regurgitation between the atria, ventricles and arteries.

Located between the left atrium and the left ventricle, the mitral valve acts like a one-way valve to ensure that blood flows from the left atrium to the left ventricle at a certain rate. The mitral valve complex is a functionally and anatomically complicated structure generally considered to consist of the valve annulus, leaflets, chordae tendineae and papillary muscles. The function of the mitral valve depends on the integrity of its physiological structure. When the mitral valve is normally closed, the two leaflets are in the same plane and abut each other tightly, completely preventing regurgitation of ventricular blood. Achieving this requires size appropriateness of the mitral valve annulus, structural intactness of the leaflets, ability of the papillary muscles to contract and pull the chordae tendineae to provide desired support to the leaflets, appropriate closing forces resulting from contraction of the left ventricular muscles and normal morphology and functionality of the ventricle. Any abnormality in any of those factors may lead to mitral regurgitation (MR).

Rheumatic heart diseases are one of the most common types of heart valve diseases. For severe valvular lesions, the only and ultimate effective treatment is heart valve replacement. Statistics show that over 100,000 heart valve replacement surgeries are performed every year in the world. With the development of cardiac surgery, heart valve replacement procedures have become routine ones. Long-term efficacy in patients undergoing heart valve replacement depends primarily on valve quality, posing a challenge for developers of replacement heart valves.

In recent years, advancements in interventional therapies have brought about rapid development and increased clinical application of catheterized delivery of artificial cardiac valves for replacement or repair, and satisfactory outcomes have been reported. With a minimally invasive interventional procedure, an artificial cardiac valve may be implanted into the heart to replace or repair a diseased native mitral valve. Such an artificial cardiac valve is mainly composed of a stent and leaflets inside the stent and can be implanted without opening the chest, leaving minimal trauma and permitting rapid postoperative recovery. This provides a new solution for patients with stenotic heart valves which exceed the ability of the current conventional therapeutic approaches to cope with to extend the patients' lives and relieve their pain.

However, due to a relatively short history of the interventional therapeutic technology, there remain many problems in its practical application nowadays. For example, some artificial cardiac valves are easy to break due to lack of support. There are some stents that could not well match the native valve anatomy and tend to lead to paravalvular leaks. There are also some stents structured to possibly compress the heart outflow tract. There are still some stents that are too long and may cause left ventricular outflow tract obstruction. Those skilled in the art are always seeking solutions to these problems with the existing artificial cardiac valves.

SUMMARY OF THE INVENTION

It is a first objective of the present invention to provide an artificial cardiac valve which solves the problem of insufficient support and easy breakage of some existing artificial cardiac valves.

It is a second objective of the present invention to provide an artificial cardiac valve which solves the problem of an unsatisfactory match between the stent and native valve anatomy which is prone to lead to displacement and paravalvular leaks arising from the use of some existing artificial cardiac valves.

It is a third objective of the present invention to provide an artificial cardiac valve which solves the problem of left ventricular outflow tract obstruction caused by long lengths of some existing artificial cardiac valves.

The above objectives are attained by an artificial cardiac valve according to the present invention, which includes: an outer stent; an inner stent nested within and connected to the outer stent; leaflets disposed inside the inner stent; and membranes attached to walls of the outer stent and the inner stent, wherein the inner stent is a cylindrical mesh tube, and the outer stent includes a first stent segment, a second stent segment and a third stent segment which are connected sequentially, the first stent segment being a mesh tube, the second stent segment being a mesh tube having a substantially D-shaped cross-section, the third stent segment being a flared mesh tube, the first stent segment having a maximum diameter that is equal to a diameter of the second stent segment, the third stent segment having a minimum diameter that is equal to the diameter of the second stent segment.

Optionally, in the artificial cardiac valve, the inner stent may be less flexible than the outer stent.

Optionally, in the artificial cardiac valve, the second stent segment may include a flat wall and a curved wall, the flat wall connecting with the curved wall to form the mesh tube having a substantially D-shaped cross-section, and wherein the third stent segment has a wall inclined at a greater angle with respect to the flat wall than with respect to the curved wall.

Optionally, in the artificial cardiac valve, the first stent segment may have a wall inclined with respect to the flat wall of the second stent segment at an angle ranging from 10 degrees to 60 degrees.

Optionally, the artificial cardiac valve may further include barbs provided on the outer stent, each of the barbs having a free end extending obliquely away from a free end of the first stent segment.

Optionally, in the artificial cardiac valve, each of the barbs may extend at the free end at an angle of 10 degrees to 80 degrees with respect to the wall of the first stent segment or of the second stent segment and have a length ranging from 3 mm to 6 mm.

Optionally, in the artificial cardiac valve, the number of the barbs may be more than one, wherein the barbs are distributed in one or more rows circumferentially around the outer stent.

Optionally, in the artificial cardiac valve, the outer stent may have a diameter of from 29 mm to 45 mm.

Optionally, in the artificial cardiac valve, the outer stent may be welded, sutured or riveted to the inner stent.

Optionally, the artificial cardiac valve may further include suture holes formed in the inner stent, wherein the leaflets are sutured onto the inner stent through the suture holes.

The artificial cardiac valve provided in the present invention includes the outer stent, the inner stent nested within and connected to the outer stent, the leaflets disposed inside the inner stent and the membranes attached to the walls of the outer and inner stents. The inner stent is a cylindrical mesh tube, and the outer stent includes, sequentially connected, the first, second and third stent segments. The first stent segment is a mesh tube. The second stent segment is a mesh tube having a substantially D-shaped cross-section, and the third stent segment is a flared mesh tube. The first stent segment has a maximum diameter that is equal to a diameter of the second stent segment and to a minimum diameter of the third stent segment. In this stent design, the inner stent can withstand traction forces from the leaflets, and the outer stent is adapted to match the anatomy of the native valve. As a result, after release, the artificial cardiac valve will seldom experience displacement and be barely associated with paravalvular leaks. Moreover, it has a prolonged service life. Additionally, the first stent segment assumes the shape of a conical frustum, which allows for a shorter overall length and thus avoids the issue of left ventricular outflow tract obstruction. Further, the outer stent is provided with barbs which can hook into the tissue around the native valve where the artificial cardiac valve is implanted, thereby anchoring the artificial cardiac valve and improving its post-release stability.

In these figures, 1—outer stent; 10—first stent segment; 11—second stent segment; 12—third stent segment; 2—leaflet; 3—membrane; 4—barb; 5—connecting member; 6—inner stent; 7—suture hole.

DETAILED DESCRIPTION

The present invention will be described in greater detail below with reference to specific embodiments which are to be read in conjunction with the accompanying drawings. Features and advantages of the invention will be more readily apparent from the following detailed description, and from the appended claims. Note that the figures are provided in a very simplified form not necessarily presented to scale, with the only intention of facilitating convenience and clarity in explaining the embodiments of the invention.

Before going into details of the present invention, a description will be given of its major principles and concepts. Studies on the problem of proneness to breakage due to insufficient support with some existing artificial cardiac valves suggest that the reason for insufficient support is that the stent serves to continually support and anchor the implanted artificial cardiac valve while being subject to repeated traction from the leaflets sutured inside the stent. Since the traction from the leaflets is opposite to the forces exerted by the stent for support and anchoring, the support does not suffice. The present invention is based just on this finding to retrofit the conventional stent design to include an outer stent and an inner stent. The leaflets are sutured inside the inner stent so that the inner stent will not only withstand the traction from the leaflets but will also relieve part of the force acting on the outer stent. The outer stent is designed to match the anatomy of the native valve to provide desired support and anchoring. Artificial cardiac valves constructed in accordance with the present invention, when deployed, will not experience displacement or be associated with paravalvular leaks and has a prolonged service life.

Figure 1:
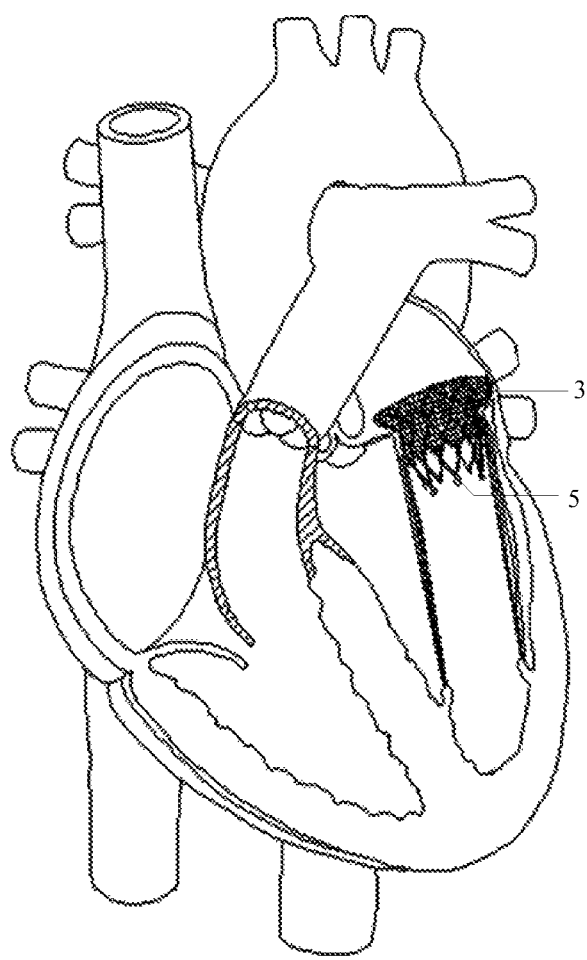
FIG. 1 schematically shows an artificial cardiac valve according to an embodiment of the present invention that has been implanted at the native mitral valve of the heart.
Figure 2:
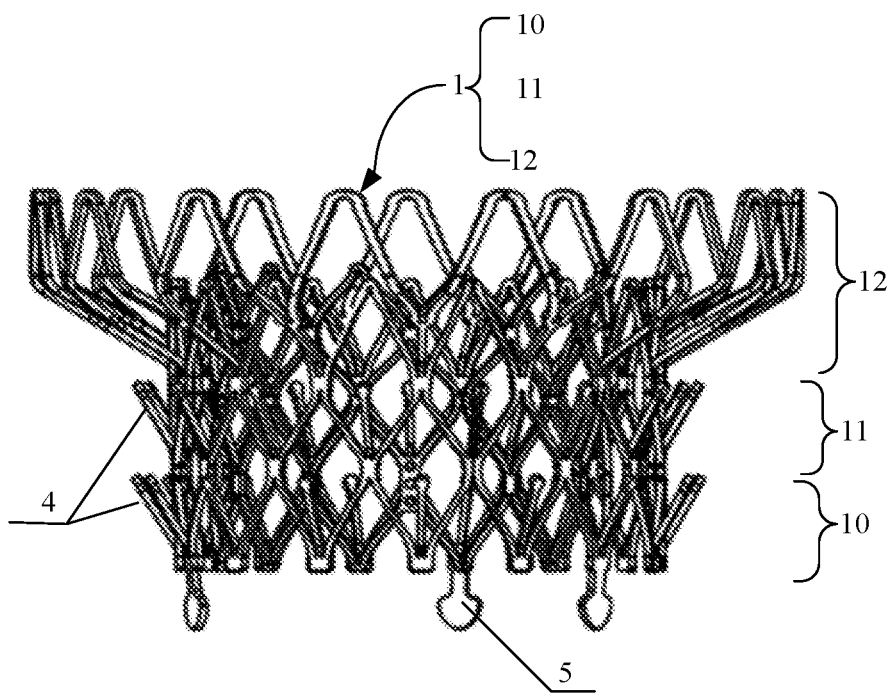
FIG. 2 is a front elevation view of an artificial cardiac valve according to an embodiment of the present invention.

FIG. 1 schematically shows an artificial cardiac valve according to the present invention that has been implanted at the native mitral valve of the heart, and FIG. 2 is a front elevation view of the artificial cardiac valve. The artificial cardiac valve includes an outer stent 1, an inner stent 6 nested within the outer stent 1 and connected to the outer stent 1, leaflets 2 disposed inside the inner stent 6 and membranes 3 attached to walls of the outer and inner stents 1, 6. The inner stent 6 is a cylindrical mesh tube. The outer stent 1 includes, sequentially connected, a first stent segment 10, a second stent segment 11 and a third stent segment 12. The first stent segment 10 is a mesh tube. The second stent segment 11 is a mesh tube having a substantially D-shaped cross-section. The third stent segment 12 is a flared mesh tube. The first stent segment 10 has a maximum diameter that is equal to a diameter of the second stent segment 11 and the third stent segment 12 has a minimum diameter that is equal to the diameter of the second stent segment 11.

The inner and outer stents 6, 1 play their own roles and thus allow for a longer service life of the artificial cardiac valve. To this end, it is required that the inner stent 6 is less flexible than the outer stent 1. That is, the inner stent 6 is required to be slightly stiffer than the outer stent 1. The outer stent 1 is stiff enough to withstand hemodynamic pressures, and the inner stent 6 is designed to be able to withstand pulling forces from the leaflets 2.

Figure 4:
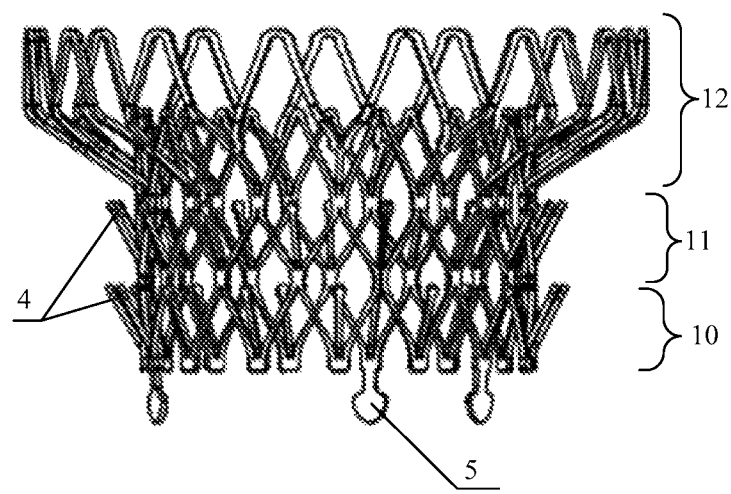
FIG. 4 is a front elevation view of an outer stent of an artificial cardiac valve according to an embodiment of the present invention.
Figure 5:
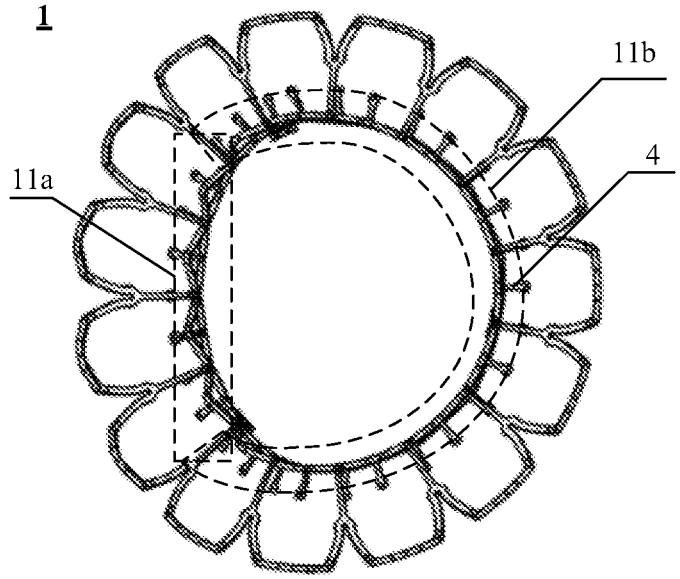
FIG. 5 is a top view of FIG. 4.

Specifically, with additional reference to FIGS. 4 and 5, the second stent segment 11 has a flat wall 11a and a curved wall 11b. The flat wall 11a is connected with the curved wall 11b to form a mesh tube having a substantially D-shaped cross-section. In this way, the cross-section of the outer stent 1 matches well with that of the space where the artificial cardiac valve is to be deployed, preventing compression of the heart outflow tract due to unreasonable contour of the outer stent 1. In order to increase conformity to anatomical contours of the native tissue and avoid damage to the tissue incurred by the structure of the third stent, the third stent segment 12 is designed such that the third stent segment 12 has a wall inclined at a larger angle with respect to the flat wall 11a than with respect to the curved wall 11b. In practice, when the artificial cardiac valve is implanted at the native mitral valve, the second stent segment 11 is located with the flat wall 11a being closer to the heart outflow tract.

In this embodiment, the outer stent 1 is coaxial with the inner stent 6 and the outer stent 1 has a length equal to or greater than the length of the inner stent 6. The inner stent 6 may be as long as the leaflets 2 can be sutured and withstand traction forces from the leaflets 2. Preferably, the diameter of the outer stent 1 ranges from 29 mm to 45 mm and that of the inner stent 6 from 25 mm to 35 mm. The outer stent 1 may be welded, sutured or riveted to the inner stent 6. The inner stent 6 may be made of a nickel-titanium alloy, a cobalt alloy, a chromium alloy or a nickel alloy. The outer stent 1 may be made of a nickel-titanium alloy, a cobalt alloy, a chromium alloy or a nickel alloy. The membranes 3 may be polytetrafluoroethylene (PTFE), polyethylene (PE) or polypropylene (PP) membranes.

Additionally, the first stent segment 10 resembles a conical frustum so that the outer stent 1 has a shorter overall length which can prevent the implanted stent from cause damage to surrounding tissues or left ventricular outflow tract obstruction due to an excessive length.

Figure 3:
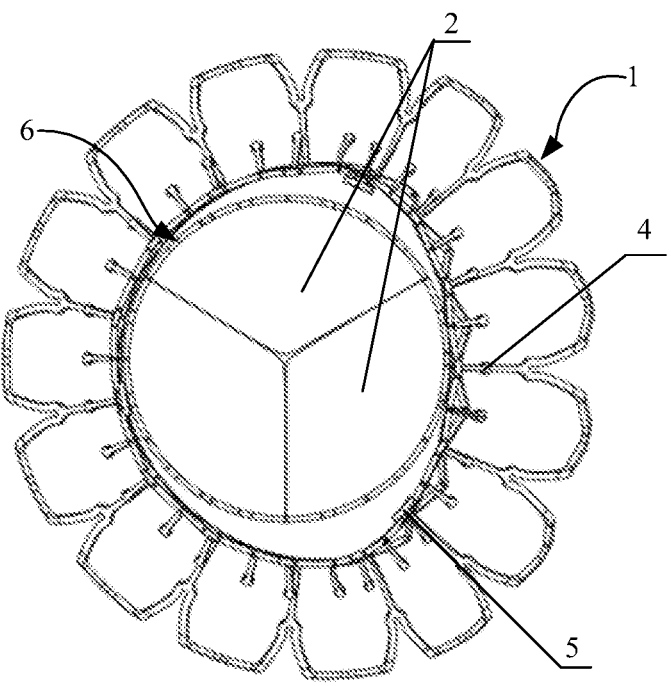
FIG. 3 is a top view of FIG. 2.

Referring to FIGS. 2 and 3, the first, second and third stent segments 10, 11, 12 are coaxial and have different shapes. Fabrication of the outer stent 1 may include providing a single original tube; laser cutting of the original tube into an original mesh tube; dividing the original mesh tube into three sections for individual shaping. The original tube may be shaped to have a substantially D-shaped cross-section to form the second stent segment 11. During the formation of the first stent segment 10, an end edge of the original tube may be radially contracted to form a conical frustum-shape. In this embodiment, the flat wall of the first stent segment 10 may be inclined with respect to the wall of the second stent segment 11 at an angle of 10 to 60 degrees, preferably 30 degrees. In order to ensure sufficient support of the artificial cardiac valve in use and prevent breakage of the stent due to inadequate support, the second stent segment 11 is preferably a cylindrical mesh tube having rhombic cells.

Referring to FIGS. 2 and 4, the outer stent 1 is provided with barbs 4. Each barb 4 has a free end extending obliquely away from the free end of the first stent segment 10. Specifically, the barbs 4 may be provided on the wall of either the first stent segment 10 or the second stent segment 11. The barbs 4 may extend relative to the wall of either the first stent segment 10 or the second stent segment 11 at angle of 10 to 80 degrees, preferably 30 degrees. The barbs 4 may each have a length of 3-6 mm. During use, the barbs 4 hook into the tissue around the valve in order to anchor the artificial cardiac valve. Here, the number of the barbs 4 may be more than one, and the multiple barbs 4 may be evenly distributed on the outer circumference of the first stent segment 10 or the second stent segment 11. In addition, they may be arranged into one or more rows around the circumference of the outer stent 1.

In this embodiment, the barbs 4 may either be integral with or welded onto the outer stent 1. Overall shape of the barbs 4 may be, but is not limited to, linear, V-like or U-like. Moreover, suitable shapes for the free end portions of the barbs 4 may include, but are not limited to, wedges and needles, as long as they can hook into the tissue around the valve to satisfactorily anchor the outer stent 1.

Specifically, the artificial cardiac valve according to this embodiment can be radially contracted and expanded. In order to achieve a close fit to the target tissue and create a lumen allowing sufficient blood flow during delivery and deployment of the artificial cardiac valve, according to the present invention, the second stent segment 11 and the third stent segment 12 constitutes a structure that well matches the anatomy of the native valve (especially the anatomy of the native tissue around the mitral valve) and can thus be self-anchored, facilitating fast release accurately at the target site. Moreover, the released stent will closely fit the lumen in shape with a minimized chance for displacement. Further, the match between the aforementioned structure and the surrounding tissue can facilitate closure by the membranes 3 and prevention of paravalvular leaks.

In practical use, the artificial cardiac valve is implanted in the patient's body while being loaded in a delivery device. When the target site is reached, the artificial cardiac valve is released, and the crimped stent in the artificial cardiac valve will immediately expand. As shown in FIG. 1, subsequent to the release of the artificial cardiac valve, the first stent segment 10 is situated in the ventricle and the third stent segment 12 in the atrium so that the third stent segment 12 acts as a blood inlet and the first stent segment 10 as a blood outlet. As the diameter of the third stent segment 12 is greater than that of the second stent segment 11, when the heart dilates, the native valve annulus will block the third stent segment 12 and prevent the artificial cardiac valve from sliding toward the ventricle. When the heart contracts, the barbs 4 will prevent the artificial cardiac valve from moving toward the atrium. Therefore, according to the present invention, with the structure of the outer stent 1, the released artificial cardiac valve can be more effectively prevented from being displaced by pressures from blood flow, i.e., its flushing effect. This can prolong the service life of the artificial cardiac valve and reduce its damage to the surrounding tissue.

Figure 6:
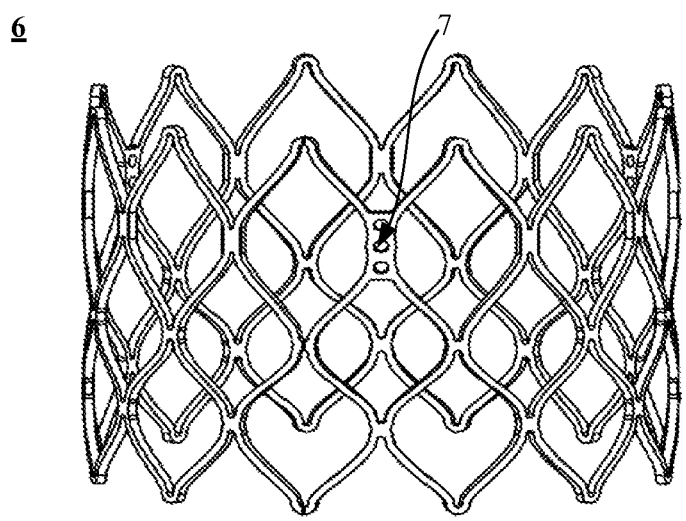
FIG. 6 is a front elevation view of an inner stent of an artificial cardiac valve according to an embodiment of the present invention.

The leaflets 2 may be distributed and shaped as shown in FIG. 3. The number of the leaflets 2 may be more than two, each having a thickness ranging from 0.2 mm to 0.5 mm. The leaflets 2 may be each fabricated from a biological tissue (e.g., porcine pericardium, bovine pericardium, porcine heart valve, bovine pericardium, etc.), a polymer material or a tissue-engineered material. Each of the leaflets 2 has a rectangular portion and an arcuate portion continuing with the rectangular portion. The leaflets 2 with such a structure can be more easily sutured and allow for good hemodynamic performance of the valve. With combined reference to FIGS. 3 and 6, in order to attach the leaflets 2 onto the stent, according to the present invention, the inner stent 6 is provided with suture holes 7, and a suture line can be inserted to suture the leaflets 2 onto the stent through the suture holes 7. Preferably, the suture line is biocompatible.

Further, with reference to FIGS. 2 and 3, in order to facilitate the engagement between the artificial cardiac valve and the delivery device during delivery, connecting members 5 may be provided at the free end of the first stent segment 10. The number of the connecting members 5 may be at least two, preferably three in the present embodiment. The three connecting members may be evenly distributed circumferentially around the first stent segment 10.

In order to facilitate anchoring of the artificial cardiac valve and enable observation of its position, the outer stent 1 and/or inner stent 6 is/are provided with tracing mark(s). In case of the outer stent 1 being connected to the inner stent 6 by riveting, a tracing mark may be provided at the rivet joint between the outer stent 1 and the inner stent 6. Specifically, the tracing mark may be created by filling a tracing medium into a hole formed at the rivet joint. The tracing medium is formed of one or more of a platinum-rhodium (Pt—Ir) alloy, platinum (Pt) and tantalum (Ta).

In summary, the artificial cardiac valve proposed in the present invention includes the outer stent, the inner stent nested within and connected to the outer stent, the leaflets disposed inside the inner stent and the membranes attached to the walls of the outer and inner stents. The inner stent is a cylindrical mesh tube, and the outer stent includes, sequentially connected, the first, second and third stent segments. The first stent segment is a mesh tube. The second stent segment is a mesh tube having a substantially D-shaped cross-section, and the third stent segment is a flared mesh tube. The first stent segment has a maximum diameter that is equal to a diameter of the second stent segment. The third stent segment has a minimum diameter that is equal to a diameter of the second stent segment. In this stent design, the inner stent can withstand traction forces from the leaflets, and the outer stent is adapted to match the anatomy of the native valve. As a result, after release, the artificial cardiac valve will seldom experience displacement and be barely associated with paravalvular leaks. Moreover, it has a prolonged service life. Additionally, the first stent segment assumes the shape of a conical frustum, which allows for a shorter overall length and thus avoids the issue of left ventricular outflow tract obstruction. Further, the outer stent is provided with barbs which can hook into the tissue around the native valve where the artificial cardiac valve is implanted, thereby anchoring the artificial cardiac valve and improving its post-release stability. The design of the through-silicon vias (TSVs) penetrating through the second semiconductor substrate and the second dielectric layer and connecting the pads in the first dielectric layer simplifies the wiring process in the existing packaging techniques and improves processing efficiency by, for example, dispensing with the need to wire the pads only after openings are formed by repeated etching. In addition, the formation of barrier layers for preventing underlying structures from being damaged during the etching processes is dispensed with. This allows for the use of a thinner carrier substrate during packaging and optimizes the performance of semiconductor devices formed on the backside of the second semiconductor substrate.

The description presented above is merely that of a few preferred embodiments of the present invention and does not limit the scope thereof in any sense. Any and all changes and modifications made by those of ordinary skill in the art based on the above teachings fall within the scope as defined in the appended claims.

What is claimed is:

1. An artificial cardiac valve, comprising:
   an outer stent;
   an inner stent nested within and connected to the outer stent;
   leaflets disposed inside the inner stent; and
   membranes attached to walls of the outer stent and the inner stent,
   wherein the inner stent is a cylindrical mesh tube, and the outer stent comprises a first stent segment, a second stent segment and a third stent segment which are connected sequentially, the first stent segment being a mesh tube, the second stent segment being a mesh tube having a substantially D-shaped cross-section, the third stent segment being a flared mesh tube, the first stent segment having a maximum diameter that is equal to a diameter of the second stent segment, the third stent segment having a minimum diameter that is equal to the diameter of the second stent segment,
   wherein the second stent segment comprises a flat wall and a curved wall, the flat wall connecting with the curved wall to form the mesh tube having the substantially D-shaped cross-section, and wherein the third stent segment has a wall inclined at a greater angle with respect to the flat wall than with respect to the curved wall.

2. The artificial cardiac valve of claim 1, wherein the inner stent is less flexible than the outer stent.

3. The artificial cardiac valve of claim 1, wherein the first stent segment has a wall inclined with respect to the flat wall of the second stent segment at an angle of from 10 degrees to 60 degrees.

4. The artificial cardiac valve of claim 1, further comprising barbs provided on the outer stent, each of the barbs having a free end extending obliquely away from a free end of the first stent segment.

5. The artificial cardiac valve of claim 4, wherein each of the barbs extends at the free end thereof at an angle of 10 degrees to 80 degrees with respect to a wall of the first stent segment or a wall of the second stent segment, and wherein each of the barbs has a length of from 3 mm to 6 mm.

6. The artificial cardiac valve of claim 4, wherein a number of the barbs is more than one, and the barbs are distributed in one or more rows circumferentially around the outer stent.

7. The artificial cardiac valve of claim 1, wherein the outer stent has a diameter of from 29 mm to 45 mm.

8. The artificial cardiac valve of claim 1, wherein the outer stent is welded, sutured or riveted to the inner stent.

9. The artificial cardiac valve of claim 1, further comprising suture holes formed in the inner stent, wherein the leaflets are sutured onto the inner stent through the suture holes.

* * * * *